United States Patent
Decker et al.

(10) Patent No.: US 10,351,485 B1
(45) Date of Patent: Jul. 16, 2019

(54) MICROBIAL PASSIVATION OF EXPLOSIVE ORDNANCE

(71) Applicant: The Board of Regents of the Nevada System of Higher Education on Behalf of the Desert Research Institute, Reno, NV (US)

(72) Inventors: David L. Decker, Reno, NV (US); Joseph J. Grzymski, Reno, NV (US)

(73) Assignee: Nevada System of Higher Education on Behalf of the Desert Research Institute, Reno, NV (US)

( * ) Notice: Subject to any disclaimer, the term of this patent is extended or adjusted under 35 U.S.C. 154(b) by 0 days.

(21) Appl. No.: 15/792,496

(22) Filed: Oct. 24, 2017

Related U.S. Application Data

(60) Provisional application No. 62/412,234, filed on Oct. 24, 2016.

(51) Int. Cl.
  *C06B 21/00* (2006.01)
  *C12R 1/00* (2006.01)
  (Continued)

(52) U.S. Cl.
  CPC ............ *C06B 21/0091* (2013.01); *C12R 1/00* (2013.01); *F02K 9/08* (2013.01); *F42B 23/00* (2013.01)

(58) Field of Classification Search
  CPC ...................................................... F42B 33/06
  (Continued)

(56) References Cited

U.S. PATENT DOCUMENTS

| 5,511,482 A | * | 4/1996 | DiPietropolo | .......... F42B 12/72 102/293 |
| 5,736,669 A | * | 4/1998 | Thomas | .................... B09C 1/10 102/293 |

(Continued)

FOREIGN PATENT DOCUMENTS

| JP | 2009/264679 | 2/2011 |
| WO | WO 2000/15306 | 3/2000 |
| WO | WO 2013/113058 | 8/2013 |

OTHER PUBLICATIONS

Department of the Army, United States of America, "Destruction of Chemical Munitions at Pueblo Chemical Depot, Colorado, Final Environmental Impact Statement, Program Manager for Chemical Demilitarization," Mar. 2002, Aberdeen Proving Ground, MD 21010-4005.

(Continued)

*Primary Examiner* — Joshua E Freeman
(74) *Attorney, Agent, or Firm* — Holland & Hart, LLP

(57) ABSTRACT

A number of devices and methods for biopassivating explosive ordnance are disclosed. In some embodiments, a biopassivation reactor device is used to render energetic material in an explosive ordnance less explosive and/or non-explosive. This can be done by coupling the biopassivation reactor device to the fuse opening of the explosive ordnance. This can also be done by incorporating the biopassivation reactor device into the explosive ordnance at the time of manufacture. The biopassivation reactor device can include a housing enclosing microorganisms, water, additives, and/or or the like. In some embodiments, an entire ordnance magazine can be operated as a bioreactor to passivate the explosive ordnance inside.

23 Claims, 4 Drawing Sheets

(51) Int. Cl.
  *F42B 23/00* (2006.01)
  *F02K 9/08* (2006.01)
(58) Field of Classification Search
  USPC .................................................. 102/287, 293
  See application file for complete search history.

(56) References Cited

U.S. PATENT DOCUMENTS

| | | | | |
|---|---|---|---|---|
| 5,763,815 | A * | 6/1998 | Thomas | B09C 1/10 102/293 |
| 6,120,627 | A * | 9/2000 | Badger | B09C 1/10 149/108.8 |
| 6,274,368 | B1 * | 8/2001 | Nicklin | C12N 9/14 435/252.1 |
| 6,334,395 | B1 * | 1/2002 | Badger | B09C 1/10 435/262.5 |
| 6,644,200 | B1 * | 11/2003 | Badger | B09C 1/10 102/288 |
| 6,660,112 | B1 * | 12/2003 | Badger | B09C 1/10 149/108.8 |
| 6,668,725 | B2 * | 12/2003 | Badger | B09C 1/10 102/289 |
| 6,936,456 | B1 * | 8/2005 | Brodman | C12N 1/20 435/252.1 |
| 7,240,618 | B2 * | 7/2007 | Badger | B09C 1/10 102/293 |
| 8,585,841 | B2 * | 11/2013 | Lubbe | C06B 21/005 149/109.6 |
| 8,618,347 | B2 | 12/2013 | Smylie et al. | |
| 8,754,284 | B2 | 6/2014 | Goodridge et al. | |
| 8,850,984 | B2 * | 10/2014 | Smylie | A62D 3/02 102/301 |
| 10,074,925 | B1 * | 9/2018 | Thomas | F42B 33/06 |
| 2002/0078849 | A1 * | 6/2002 | Badger | B09C 1/10 102/293 |
| 2004/0250674 | A1 | 12/2004 | Badger et al. | |
| 2006/0030025 | A1 * | 2/2006 | Riggs | C06B 21/0091 435/262.5 |
| 2009/0038496 | A1 * | 2/2009 | Maegerlein | F42C 15/38 102/222 |
| 2011/0041718 | A1 * | 2/2011 | Lubbe | C06B 21/005 102/200 |
| 2011/0052537 | A1 * | 3/2011 | Craig | B09C 1/10 424/93.3 |
| 2011/0155500 | A1 * | 6/2011 | Smylie | A62D 3/02 181/116 |
| 2012/0282680 | A1 * | 11/2012 | Goodridge | A62D 3/02 435/262.5 |
| 2012/0308433 | A1 | 12/2012 | Adams | |
| 2015/0118692 | A1 * | 4/2015 | Johnson | C08L 83/04 435/7.5 |

OTHER PUBLICATIONS

Tavares et al., "Overview of Demilitarization Techniques," ADAI—University of Coimbra, Greener and Safer Energetic and Ballistic Systems, 2015, Bucharest.
Poulin, Isabelle, "Literature Review on Demilitarization of Munitions," Technical Memorandum, DRDC Valcartier TM 2010-213, Defense Research and Development, Nov. 2010, Canada.
Government of the Netherlands, "Best Practice Guide on the Destruction of Conventional Ammunition," Jun. 2, 2008, Netherlands.
Kalafut, T. el al., "Biotransformation patterns of 2,4,6-trinitrotoluene by aerobic bacteria." Current Microbiology 36, 45-54, (1998).
Vorbeck, C. et al., "Identification of a hydride-Meisenheimer complex as a metabolite of 2,4,6-trinitrotoluene by *Mycobacterium* strain." J. Bacteriology 176, 932-934 (1994).
Fernando, T. et al., Biodegradation of TNT (2,4,6-trinitrotoluene) by Phancrochaete chrysosporium. Applied and Environmental Microbiology 56, 1666-1671 (1990).
Hawari, J. et al. "Biotransformation of 2,4,6-trinitrotoluene with Phanerochaete chrysosporium in agitated cultures at pH 4.5." Applied and Environmental Microbiology 65, 2977-2986 (1999).
Scheibner, K. et al., "Screening for Fungi Intensively Mineralizing 2,4,6-trinitrotoluene," Applied Microbiology Biotechnology 47, 452-457 (1997).
Fiorella, P. D. et al., "Transformation of 2,4,6-Trinitrotoluene by Pseudomonas pseudoalcaligenes JS52," Applied and Environmental Microbiology 63, 2007-2015 (1997).
Martin, J. L. et al., "Denitration of 2,4,6-trinitrotoluene by Pseudomonas Savastanoi," Can. J. Microbiol. 43, 447-455 (1997).
Zhao, J.-S., et al., "Biodegradation of Hexahydro-1,3,5-Trinitro-1,3,5-Triazine and its Mononitroso Derivative Hexahydro-1-Nitroso-3,5-Dinitro-1,3,5-Triazine by *Klebsiella pneumoniae* Strain SCZ-1 Isolated from an Anaerobic Sludge," Applied and Environmental Microbiology 68, 5336-5341 (2002).
Zhao, J-S., et al., "Metabolism of Hexahydro-1,3,5-Trinitro-1,3,5-Triazine Through Initial Reduction to Hexahydro-1-Nitroso-3,5-Dinitro-1,3,5-Triazine Followed by Denitration in Clostridium Bifermentans HAW-1," Applied Microbiology Biotechnology 63, 187-193 (2003).
Zhao, J-S., et al., "Phylogenetic and Metabolic Diversity of Hexahydro-1,3,5-Trinitro-1,3,5-Triazine (RDX)-Transforming Bacteria in Strictly Anaerobic Mixed Cultures Enriched on RDX as Nitrogen Source," FEMS Microbiology Ecol. 46, 189-196 (2003).
Zhao, J-S. et al., "Phylogeny of Cyclic Nitramine-degrading Psychrophilic Bacteria in Marine Sediment and their Potential Role in the Natural Attenuation of Explosives," FEMS Microbiology Ecol. 49, 349-357 (2004).
Young, D. M., et al., "Biotransformation of Hexahydro-1,3,5-trinitro-1,3,5-triazine (RDX) by a Prospective Consortium and its Most Effective isolate Serratia Marcescens," Biotechnology and Bioengineering 53, 515-522 (1997).
Purde, I. B. et al., "The Use of Enterobacter Cloacae ATCC 43560 in the Development of a two-phase Partitioning Bioreactor for the Destruction og Hexahydro-1,3,5-trinitro-1,3,5-s-triazine (RDX)," J. Biotechnology 100, 65-75 (2003).
Boopathy, R. et al., "Metabolism of Explosive Compounds by Sulfate-Reducing Bacteria," Curr Microbiol 37, 127-131 (1998).
Regan, K. M., et al., "Characterization of Clostridium Bifermentans and its Biotransformation of 2,4,6-trinitrotoluene (TNT) and 1,3,5-triaza-1,3,5-trinitrocyclohexane (RDX)," Biotechnology Letters 16, 1081-1086 (1994).
Bhushan, B. et al., "Chemotaxis-mediated Biodegradation of Cyclic Nitramine Explosives RDX, HMX, and CL-20 by *Clostridium* sp," EDB2. Biochemical and Biophysical Research Communications 316, 816-821 (2004).
Vanderberg, L. A., "Catabolism of 2,4,6-trinitrotoluene by *Mycobacterium vaccae*," Applied Microbiology Biotechnology 43, 937-945 (1995).

* cited by examiner

MICROBIAL PASSIVATION OF EXPLOSIVE ORDNANCE

CROSS-REFERENCE TO RELATED APPLICATION

The present application claims priority through, and incorporates by reference, the applicant's prior provisional patent application entitled Microbial Munitions Passivation, Ser. No. 62/412,234, filed Oct. 24, 2016.

BACKGROUND OF CERTAIN ASPECTS OF THE DISCLOSURE

Disposal of surplus ordnance represents a significant problem for the Department of Defense. As new weapon systems are developed and enter service, these systems are acquired in mass quantities to comply with combat readiness requirements. Obsolete ordnance must then be disposed of by various means, including use in training, use in conflict, and destruction. Regardless of disposal method, the explosive components in ordnance must be rendered completely inert and no longer an explosive. The most common method to dispose of surplus ordnance by destruction is open-burn, open-detonation (OBOD). Ordnance to be disposed by OBOD is placed in a shallow pit and burned or detonated. While effective at large-scale and cost-effective disposal, OBOD may not be compliant with environmental regulations. Further, environmental regulations are changing such that OBOD will not be permissible in the future.

Recognizing the limitations of OBOD due to environmental compliance requirements, prototype incineration facilities have been designed and built to burn ordnance in a contained system, thereby preventing the release of pollutants into the environment. These facilities are equipped with filters and scrubbers that clean the gases emitted by the combustion process and remove any contaminants. Although this process is effective from an environmental compliance perspective, it is not practical due to complexity and cost compared to OBOD. In particular, such facilities treat ordnance articles one-at-a-time, a disposal rate that is far too small against the need to dispose of many thousands of articles.

The problem of disposal and passivating ordnance extends beyond surplus ordnance to other types of ordnance such as mines, which include sea-mines and landmines. Landmines maim or kill countless civilians every year in areas that were sown with landmines during previous or ongoing conflicts. Thousands of square miles of arable land are affected, contributing to the ongoing poverty of people in these areas, and to the nurturing environment for terror groups.

A modern landmine is notoriously difficult to detect and dispose of due to the parts being made mostly of plastic. This also makes them resistant to environmental degradation. They can persist as an operable device for many decades. While deployed on a much smaller scale than landmines, sea-mines are similarly difficult to detect and have long operable lives. A great deal of research and development effort has been, and continues to be, expended on developing ways to detect and dispose of mines.

There has been at least one attempt to use microorganisms to biopassivate the energetic material in explosive ordnance. It involved incorporating a bioreactor into the artillery shell or landmine at the time of manufacture. In the case of the artillery shell, the bioreactor is activated when the shell is fired. If the shell fails to explode, then the microorganisms in the bioreactor are released to passivate the energetic material. In the case of the land mine, the bioreactor is activated after a given amount of time to passivate the energetic material and render the landmine harmless.

This attempt at biopassivation of explosive ordnance suffered from a number of problems. One problem is that it was limited to fired, but unexploded artillery shells and landmines and only to situations where the bioreactor is incorporated into these munitions at the time of manufacture. It offered no solution to the disposal of surplus ordnance. It offered no solution to the problem of passivating surplus unfired ordnance manufactured without an integral bioreactor. Another problem is that it failed to account for toxic materials in the energetic material such as heavy metals that prevent or inhibit the growth of the microorganisms.

Yet another problem associated mainly with the artillery shell concept is that the bioreactor and the microorganisms inside it are subjected to extreme forces during the firing sequence of the artillery shell. These forces are likely to frequently damage or potentially even destroy the microorganisms and render the bioreactor ineffective.

BRIEF SUMMARY OF SOME ASPECTS OF THE DISCLOSURE

The inventors have therefore developed a number of embodiments of devices and methods that can be used to biopassivate explosive ordnance or munitions. An objective of such devices and methods is to protect public health and safety from the risks associated with OBOD surplus ordnance disposal methods while reducing disposal costs. Another objective is to eliminate the long-term effects on public health and safety from land- and sea-mines deployed in future conflicts. In some embodiments, one or more of these objectives are achieved by exposing the energetic material in the explosive ordnance to microorganisms that can break it down and render it less explosive and/or non-explosive.

In some embodiments, a biopassivation reactor device is used to passivate the explosive ordnance. The biopassivation reactor device can include microorganisms and water as well as other materials and components such as additives, a controller, and the like. The various components can be present in separate chambers or compartments in the biopassivation reactor device. For example, the water and the microorganisms can be in separate chambers that prevent them from mixing and initiating microorganism growth. The additives, controller, and other components can also be present in separate chambers. Alternatively, the components can be kept separate or combined in the same chamber in any combination.

The biopassivation reactor device can include a chelating agent that reduces the toxicity of the energetic material. The chelating agent reacts with metals in the energetic material to form stable, non-toxic complexes. In this way, the chelating agents neutralize or at least reduce the toxic effect of the metals on the microorganisms. This increases the growth rate and biopassivation effectiveness of the microorganisms.

In some applications, the biopassivation reactor device can be coupled to the explosive ordnance after it has been manufactured or it can be integrated into the explosive ordnance at the time of manufacture. In the former situation, the biopassivation reactor device can be coupled to the explosive ordnance at the time of disposal or at any other suitable time. In some instances, the explosive ordnance includes a fuze opening and the biopassivation reactor device is coupled to the fuze opening. In the latter situation, the biopassivation reactor device can be positioned inside explosive ordnance such as mines when they are manufactured.

The biopassivation reactor device can be used in a number of different ways depending upon a given situation. In some embodiments, a method for biopassivating explosive ordnance includes activating the biopassivation reactor device and coupling it to the explosive ordnance. Activating the biopassivation reactor includes combining at least the water and the microorganisms in the device to initiate microorganism growth. The biopassivation reactor device can be activated before or after it is coupled to the explosive ordnance.

In some applications, a method for biopassivating explosive ordnance includes manufacturing the explosive ordnance with the biopassivation reactor device as an integral component. One example of this is a mine that includes the biopassivation reactor device as an integral component. The biopassivation reactor device can include a controller that can be activated remotely later. The operative mechanism of the controller can be mechanical, electrical, or electromechanical. In some embodiments, the controller is activated using a built-in delay mechanism. For example, the controller can be configured to activate the biopassivate reactor device after a set amount of time.

Another method can include biopassivating the contents of an entire ordnance magazine all at the same time. This may be desirable in situations where the ordnance magazine includes unstable or partially unstable energetic material. The method includes introducing microorganisms into the ordnance magazine and controlling the environmental conditions inside to facilitate their growth. In some embodiments, this can include controlling parameters inside the ordnance magazine such as temperature, humidity, oxygen content, and the like.

The term "explosive ordnance" is used to refer to any munition, weapon delivery system, or ordnance item that contains an explosive material, propellant, and/or chemical agent. The term "unexploded ordnance" is used to refer to an explosive ordnance that has been primed, fuzed, armed, or otherwise prepared for action, and has been fired, dropped, launched, projected, or placed in such a manner as to constitute a hazard to operations, installation, personnel, or material and that remains unexploded either by malfunction, design, or any other cause. The terms "passivate" and "passivation" are used to refer to the conversion or transformation of an explosive material into a different chemical material that is less explosive and/or non-explosive. The terms "biopassivate," "biopassivating," and "biopassivation" are used to refer to passivation by the action of microorganisms.

This Brief Summary is provided to introduce a selection of concepts in a simplified form that are further described below in the detailed description. There are further novel features, and they will become apparent a this specification proceeds.

The Summary and the Background therefore are not intended to identify key concepts or essential aspects of the disclosed subject matter, nor should they be used to constrict or limit the scope of the claims. For example, the scope of the claims should not be limited based on whether the recited subject matter includes any or all aspects noted in the summary and/or addresses any of the issues noted in the background.

BRIEF DESCRIPTION OF THE DRAWINGS

The preferred and other embodiments are disclosed in association with the accompanying drawings in which:

FIG. 2 shows the biopassivation reactor device just before it is coupled to the explosive ordnance. FIG. 3 shows the biopassivation reactor device coupled to the fuze opening of the explosive ordnance.

FIG. 2 shows the biopassivation reactor device just before it is coupled to the solid rocket motor. FIG. 3 shows the biopassivation reactor device coupled to the solid rocket motor.

DETAILED DESCRIPTION

Figure 1:
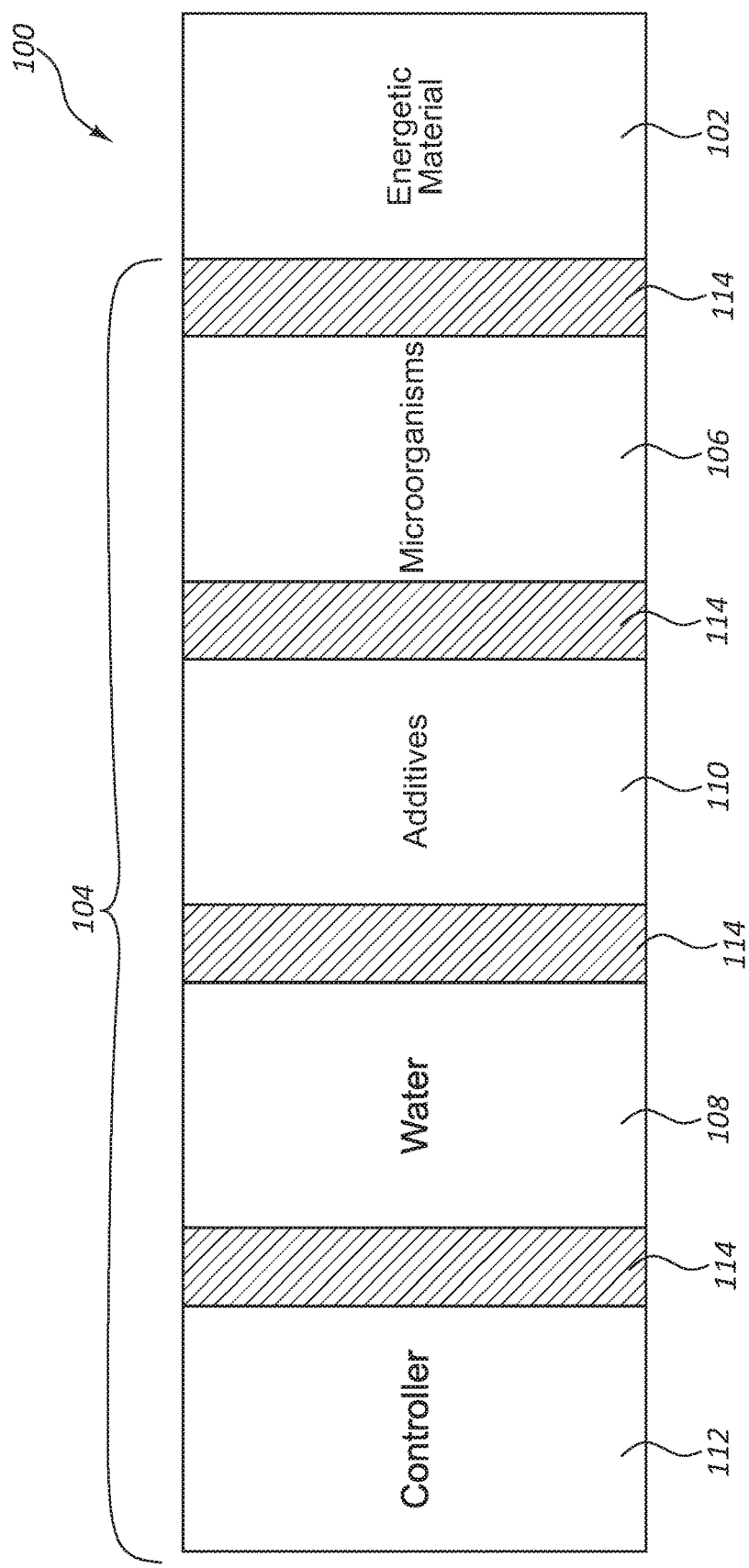
FIG. 1 is a schematic illustration of one embodiment of a biopassivation reactor device that can be used to biopassivate energetic material.

FIG. 1 shows a schematic illustration of one embodiment of a biopassivation system 100. The system 100 includes energetic material 102 positioned in operational communication with a biopassivation reactor device 104. The energetic material 102 is depicted by itself, but it is typically part of an explosive ordnance.

The biopassivation reactor device 104 includes a housing forming four separate chambers or compartments 106, 108, 110, 112 separated by barriers, dividers, or isolators 114. The chambers 106, 108, 110, 112 include microorganisms, water, additives, and a controller, respectively. The chambers 106, 108, 110, 112 separate the various materials from each other to keep the biopassivation reactor device 104 in a deactivated state.

The microorganisms can be any single microorganism or combination of microorganisms that can reduce the explosive and/or environmental risk posed by the energetic material 102. In some embodiments, the microorganisms convert the energetic material 102 into less explosive or non-explosive materials. In other embodiments, some of the microorganisms convert the energetic material 102 into intermediate materials that other microorganisms then convert into less explosive and/or non-explosive materials.

Microorganisms are advantageous because they can oxidize almost limitless sources of high-energy carbon products to derive energy for growth. These compounds include common solid energetic materials 102 such as explosive materials and propellants. Some energetic materials 102, especially propellants, include explosive materials and/or combustible metals such as aluminum, magnesium, and beryllium. The energetic materials 102 can also include: oxidizers such as ammonium nitrate, ammonium perchlorate, and potassium perchlorate; burn rate modifiers such as aluminum, beryllium, copper, iron, and lead; and various binders, plasticizers, and stabilizers such as diethylphthalate, diphenylamine, synthetic rubber, hydrocarbon polymer, and asphalt.

The microorganisms are especially desirable candidates to safely consume and passivate explosive ordnance. The organic energetic compounds 102 provide high-density, high-biochemical-reaction-energy that can readily sustain microorganism activity and growth under the correct conditions and when placed in proper contact with the energetic material 102.

Microbial degradation of energetic material 102 can occur in a broad group of aerobic and anaerobic microbes given the high nitrogen content and favorable yields of their oxidation. Table 1 below contains a non-exhaustive list of microorganisms capable of biopassivating certain energetic materials 102.

TABLE 1

Examples of Microorganisms Capable of Biopassivating Nitrosamine Energetic Materials

| Energetic Material | Bacteria | Fungi |
| --- | --- | --- |
| RDX | *Klebsiella* | |
| | *Enterobacter* | |
| | *Escherichia* | |
| | *Shewanella* | |
| | *Desulfovibrio* | |
| | *Clostridium* | |
| HMX | *Desulfovibrio* | |
| | *Clostridium* | |
| CL-20 | *Clostridium* | |
| TNT | *Bacillus* | |
| | *Mycobacterium* | |
| | *Pseudomonas* | |
| | | *Phanerochaete* |
| | | *Aspergillus* |
| | | *Fusarium* |
| | | *Mucor* |
| | | *Neurospora* |
| | | *Penicillium* |
| | | *Rhizoctonia* |

The microorganisms can be dried or induced into spore formation before being put in the biopassivation reactor device 104 to render them stable and largely inert for long periods of time. This can be done using heated air or by other processes such as lyophilization (i.e., freeze-drying). In some embodiments, a desiccant is included in the chamber 106 with the microorganisms to absorb any moisture in the chamber 106. This helps prevent the microorganisms from being activated prematurely.

Besides possessing the capability to biopassivate the energetic material 102, preferred microorganisms are those that can tolerate the drying process and/or remain viable for long periods of time with no water or media. Examples of microorganisms having these properties include spores from the genera *Bacillus* and *Clostridium*. Other exemplary microorganisms are those that can tolerate potentially toxic materials in the energetic material 102. Examples of toxic materials include metals such as lead, beryllium, aluminum, copper, iron, and the like.

The microorganisms should be capable of growing to substantial cell densities with no additional media requirements beyond that provided in the biopassivation reactor device 104 and by the energetic material 102. It should be appreciated that the biopassivation reactor device 104 can be sized to provide sufficient media (water, nutrients, and like) for a given quantity of energetic material 102. Accordingly, the size of the biopassivation reactor device 104 can be increased to accommodate large explosive ordnance and decreased to accommodate small explosive ordnance.

The biopassivation reactor device 104 can include any suitable number and type of additives. In general, the additives are optional components that are included to facilitate microorganism growth. In some embodiments, the additives include additional media that is designed to promote microorganism growth. Examples of such media include agar (various), thioglycolate broth, yeast extracts, and the like.

In some embodiments, the additives include a number of nutrients that facilitate and promote microorganism growth. It should be appreciated that any individual nutrient or combination of nutrients can be included in the biopassivation reactor device 104. Examples of suitable nutrients include the energetic compound being passivated, and any number of suitable sources of carbon, nitrogen, phosphorous, iron and other minerals.

In some embodiments, the additive may be a complementary microorganism—added to the reactor to provide syntrophic benefits to the microorganism that is degrading the energetic material. In this embodiment one organism provides the other organism a material it cannot synthesize—this mutual benefit can extend the lifetime of microorganism growth.

In other embodiments, the additives include one or more chelating or sequestering agents that are included to reduce the toxicity of the energetic material 102. The chelating agents form stable complexes with metals in the energetic material 102, rendering it less toxic and/or non-toxic to the microorganisms.

A typical chelating agent has a ring-like center which forms at least two bonds with the metal ion. Suitable chelating agents include organic and inorganic compounds. The chelating agent can be specifically selected to bind with a certain metal in the energetic material 102. For example, specific chelating agents can be used to bind with iron, lead, aluminum, and other metals commonly found in the energetic material 102. An example of a potentially suitable chelating agent is calcium disodium EDTA, but there are many potential chelating agents that would be suitable.

The controller is used to activate the biopassivation reactor device 104, which typically means breaking or otherwise removing the barriers 114 between the chambers 106, 108, 110 to allow rehydration and growth of the microorganisms. This can be accomplished using mechanical, electromechanical, or electrical components that break or otherwise breach the barriers 114 between the chambers 106, 108, 110 in the biopassivation reactor device 104.

The barriers 114 can be made of any suitable material capable of being perforated, broken, or otherwise breached by action of the controller. Examples of materials that can be used to form the barriers 114 include glass, membranes, and the like, although differing materials can be used to make different barriers 114 as well. Preferably, the properties of the barriers 114 are sufficiently robust to provide an effective and resilient barrier that is resistant to being breached during routine handling but that is not so robust that it is incapable of being effectively breached by the controller.

In some embodiments, the biopassivation reactor device 104 includes a battery or other power source that provides power to any electrical components and/or devices used to break or breach the barriers 114.

In some embodiments, the biopassivation reactor device 104 includes a purely mechanical controller. In this embodiment, the controller can be something as simple as a switch that is accessible on the exterior of the biopassivation reactor device 104. The user can actuate the switch to break the barriers 114 between the chambers 106, 108, 110 and activate the device 104.

In other embodiments, the biopassivation reactor device 104 includes an electromechanical controller. In this embodiment, the controller includes a power source that is used to drive one or more mechanical components that break/remove the barriers 114 between the chambers 106, 108, 110.

In yet other embodiments, the biopassivation reactor device 104 includes a purely electrical controller. In this embodiment, the controller includes a power source that is used to break/remove the barriers 114 between the chambers 106, 108, 110. This can be accomplished in a variety of ways. For example, a voltage or current can be applied to the barriers 114 between the chambers 106, 108, 110 to perforate them and/or otherwise allow the materials inside the chambers 106, 108, 110 to mix.

The controller can be configured to operate in any of a number of ways. In some embodiments, the controller can be manually actuated either locally or remotely to activate the biopassivation reactor device 104. In other embodiments, the controller can be configured to automatically activate the biopassivation reactor device 104 when certain criteria are met. For example, the controller can be configured to activate the biopassivation reactor device 104 after a set amount of time has passed.

The latter configuration is especially suitable for use with mines and other types of ordnance that are difficult or dangerous to retrieve after being deployed. The controller can be configured to activate the biopassivation reactor device 104 after a set amount of time such as a few days to a few years or even decades. In some embodiments, the controller includes a clock mechanism that can be used to initiate biopassivation. In other embodiments, the controller can include dissolvable barriers 114 that are configured to dissolve after a set amount of time.

It should be appreciated that these are only a few of the ways the controller can be configured to operate. There are numerous other ways the controller can be configured so long as it effectively activates the biopassivation reactor device 104.

The biopassivation reactor device 104 can be configured as a single use device or a multi-use device. A single use device can be made of lower cost materials that are easily and readily disposable. For example, the device can be made largely or entirely out of plastic or other low-cost material. A multi-use device can be made of higher quality materials that make it robust and capable of withstanding multiple uses. The device can be rebuilt or rehabilitated between uses or repeatedly used as is after each use. In some embodiments, the biopassivation reactor device 104 includes a reusable housing configured to receive and hold a disposable cartridge containing the microorganisms, water, and/or other components. Numerous other configurations are also possible.

Figure 2:
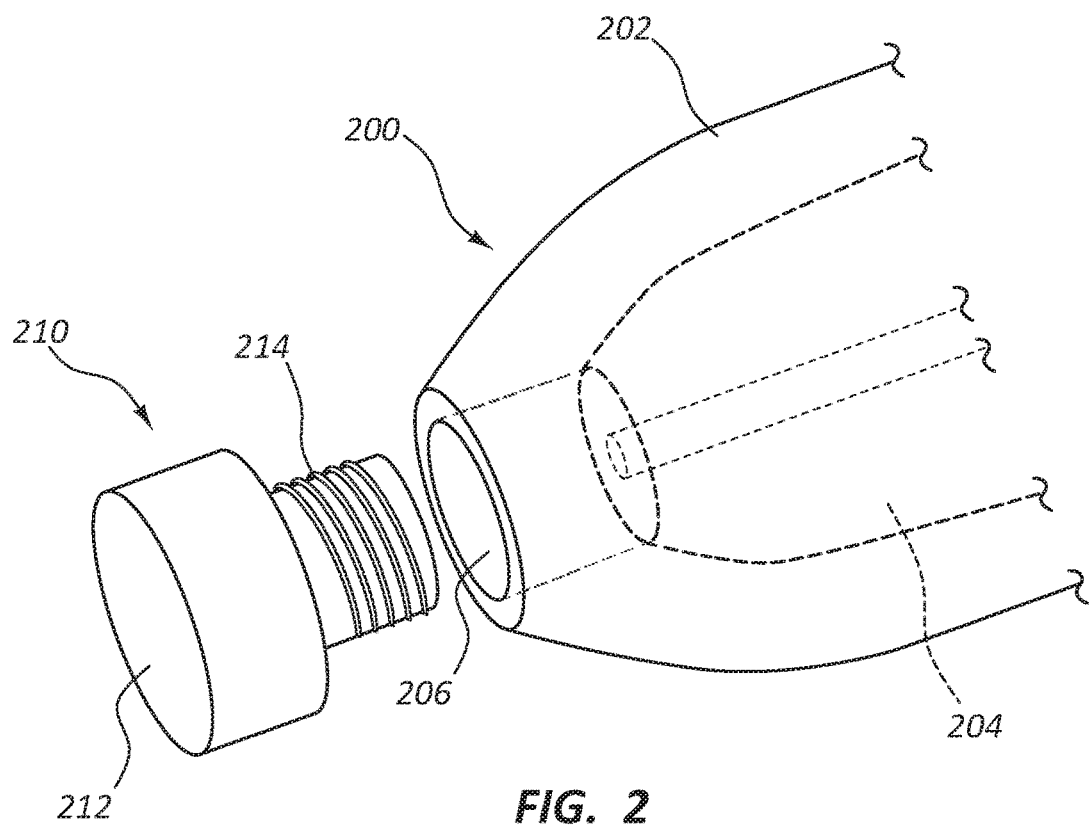
FIGS. 2-3 show perspective views of another embodiment of a biopassivation reactor device that can be coupled to the fuze opening of an explosive ordnance.
Figure 3:
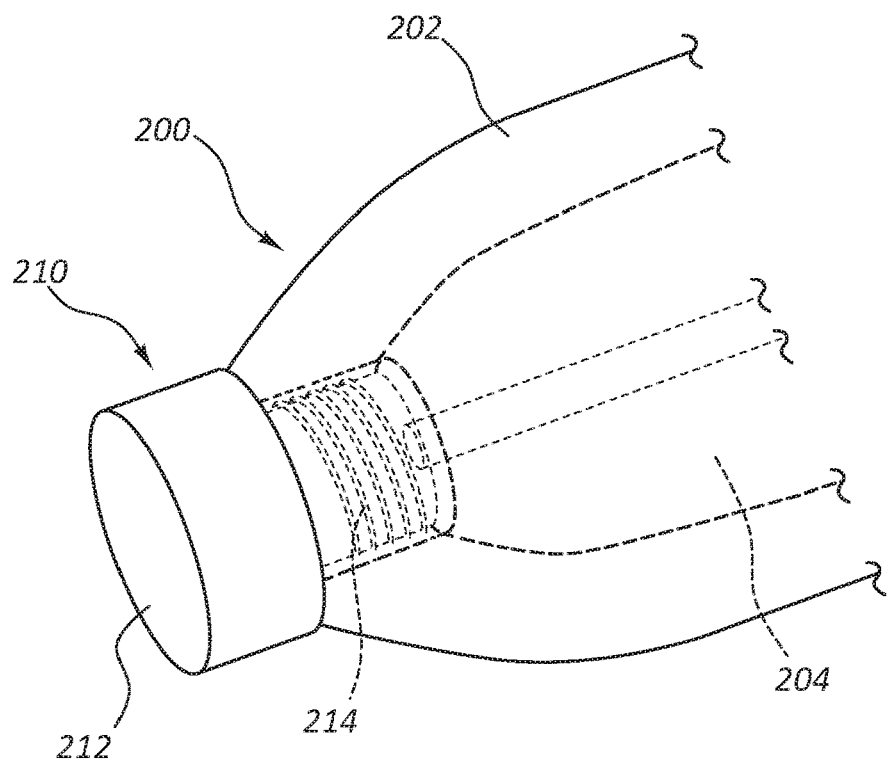

FIGS. 2-3 show perspective views of another embodiment of a biopassivation reactor device 210 including a housing 212 and a coupler 214. The housing 212 encloses and/or forms the chambers 106, 108, 110, 112. It should be appreciated that the housing 212 can have any suitable shape, size, configuration, and/or other physical dimensions, properties. Also, the housing 212 can be made of any suitable material such as metal, ceramic, plastic, combinations of these, and the like.

The explosive ordnance 200 includes an outer casing 202, energetic material 204, and a fuze opening 206. The biopassivation reactor device 210 is configured to be coupled to the fuze opening 206 of the explosive ordnance 200. The coupler 214 is configured in a manner that is complementary to the fuze opening 206. This makes it possible to fasten the coupler 214 to the fuze opening 206 to provide the microorganisms access to the energetic material 204.

In the embodiment shown in FIGS. 2-3, the coupler 214 and the fuze opening 206 are coupled together using corresponding threads that engage each and securely hold the two components together. It should be appreciated, however, that numerous other fastening devices and/or techniques can be used to couple the biopassivation reactor device 210 to the fuze opening 206. Typically, the coupler 214 is configured to be fastened to the fuze opening 206 in the same way a fuze would be coupled to the fuze opening 206. In other words, the design of the fuze dictates the configuration of the coupler 214. Regardless, the coupler 214 and/or the fuze opening 206 can be coupled together using any suitable fastening device and/or fastening technique.

The explosive ordnance 200 can be any type or size of explosive ordnance. In the past century, all shapes, sizes, and types of explosive ordnance 200 have been developed, acquired and used in the U.S. Examples of common types of explosive ordnance 200 include, rockets, guided missiles, artillery shells, mortars, projected grenades, bombs, and the like. Explosive ordnance 200 can also include solid rocket and missile motors.

Fused explosive ordnance 200 includes the fuse opening 206. For safety reasons, the fuse is only coupled to the explosive ordnance 200 when it is armed and ready to be used.

In general, the fuze (also referred to as an initiator) is the device or component used to initiate an explosion or explosive sequence in the explosive ordnance 200. The fuze can include explosive material or be devoid or substantially devoid of explosive material.

Fuze opening 206 provides ready access to the energetic material in explosive ordnance 200, and is thus the means to initiate and facilitate a microbial reaction that leads to passivation of the energetic material.

In some embodiments, the fuze includes a primary explosive material provided to initiate a secondary explosive material in the explosive ordnance. The primary explosive material can be any of those materials disclosed above. The fuze can also include an explosive booster, for example to detonate large explosive charges.

In other embodiments, the fuze can include no explosive material. Regardless whether the fuze includes explosive material, it can include electrical and/or mechanical components configured to signal or actuate ignition of the explosive material in the explosive ordnance 200. The fuze can also include safety and arming mechanisms that prevent premature or accidental detonation. For example, an artillery fuze's battery can be configured to be activated by the high acceleration experienced when it is launched and/or the rapid spinning experienced during flight. In other examples, the explosive ordnance can include mechanical shutters that isolate the fuze from the main charge until the explosive ordnance is fired.

In general, the fuze can have any suitable configuration capable of igniting the explosive ordnance 200. In some embodiments, the fuze can be a sophisticated ignition device incorporating a variety of mechanical and/or electronic components—e.g., a proximity fuze for an artillery shell, magnetic/acoustic fuze on a sea mine, spring-loaded grenade fuze, pencil detonator, or anti-handling device. In other embodiments, the fuze can be a simple burning fuse.

The term "fuze," spelled with a "z," is used broadly to refer to any type of device or component that is used to ignite the explosive material in the explosive ordnance. The term "fuse," spelled with an "s," is used to refer to a cord that is used to transmit a flame to the explosive material. A fuse typically includes a cord or rope made of readily combustible material that may or may not have gunpowder or explosive material incorporated into it.

The explosive ordnance 200 can also include any suitable energetic material 204. The energetic material 204 can be divided schematically into two categories: explosive material and propellant. These materials, if properly initiated, will produce large volumes of gas over a short period of time. The main difference between an explosive material and a propellant is the reaction rate. Explosive materials react rapidly creating a high-pressure shock wave or explosion. Propellants react at a slower rate creating a sustained lower pressure.

An explosion is a type of spontaneous chemical reaction that, once initiated, is driven by both a large exothermic change (large quantity of heat is released) and a large positive entropy change (large quantity of gases is released) in going from reactants to products, thereby constituting a thermodynamically favorable process in addition to one that propagates very rapidly. Accordingly, an explosive material is a substance that contains a large amount of energy stored in chemical bonds.

The energetic stability of the gaseous products produced by an explosion is due to the formation of strongly bonded species like carbon monoxide, carbon dioxide, and (di) nitrogen, which contain strong double and triple bonds. Consequently, most explosive materials are organic compounds containing —$NO_2$, —$ONO_2$ and —$NHNO_2$ groups that, when ignited, release gases such as those mentioned. Examples of common explosive materials are shown in Table 2 below.

TABLE 2

Examples of Common Secondary Explosive Materials

| Molecular Group | Common Name | Chemical Name |
|---|---|---|
| Nitroaromatic compounds | TNT | 2,4,6-trinitrotoluene |
| | 2,4-DNT | 2,4-dinitrotoluene |
| | Tetryl | 2,4,6-trinitrophenylmethylnitramine |
| | TATB | 1,3,5-triaminotrinitrobenzene |
| | Picric Acid | 2,4,6-trinitrophenol |
| Nitrate Esters | NC | Nitrocellulose |
| | PETN | Pentaerythritol tetranitrate |
| | NG | Nitroglycerin |
| | EGDN | Ethyleneglycol dintrate |
| Nitramines | RDX | Hexahydro-1,3,5-trinitro-1,3,5-triazine |
| | HMX | Octahydro-1,3,5,7-tetranitro-1,3,5,7-tetrazocine |
| | CL-20 | 2,4,6,8,10,12-hexanitro-2,4,6,8,10,12-hexaazaisowurtzitane |
| | NGu | Nitroguanidine |
| Azides | GAP | Glycidyl azide polymer |

Explosive materials can be grouped into three classes of compounds: inorganic compounds, organic compounds, and binary explosives that are mixtures of one or more oxidizable materials that are not explosive when separate. Inorganic compounds include lead azide, ammonium nitrate, and the like. Organic compounds include: (a) nitrate esters, such as nitroglycerine and nitrocellulose (b) nitro compounds, such as TNT and Explosive D, (c) nitramines, such as RDX and HMX, (d) nitroso compounds, such as tetrazene, and (e) metallic derivatives, such as mercury fulminate and lead styphnate, and the like. Binary explosives include mixtures of fuels and oxidizing agents and other similar mixtures.

The properties of each class of explosive material are utilized to make an explosive charge or "explosive train." In general, an explosive charge is a measured quantity of an explosive material, which may be composed of a single ingredient or a combination of two or more ingredients. An explosive train is a succession of igniting explosive materials arranged to produce an explosion. One example of an explosive train is the initiation by a firing pin of a priming composition that detonates a charge of lead azide. The lead azide initiates the detonation of a booster charge of tetryl. The tetryl in turn detonates the surrounding bursting or main charge of TNT.

An explosive material can also be categorized by the velocity of the explosion it produces. A material that detonates—i.e., the front of the chemical reaction moves faster through the material than the speed of sound—is said to be a "high explosive" and a material that deflagrates—i.e., subsonic combustion propagating through heat transfer—is said to be a "low explosive." While these definitions are distinct, the problem of precisely measuring rapid decomposition can make practical classification of an explosive material difficult.

A high explosive material is characterized by its extremely rapid decomposition rate. When a high explosive material is initiated, it decomposes almost instantaneously, a process called detonation. A detonation is a reaction that proceeds through the reacted material toward the unreacted material at a supersonic velocity.

The high explosive material can detonate with an explosive velocity ranging from 3 to 9 km/s. For example, TNT has a detonation (burn) rate of approximately 5.8 km/s (19,000 feet per second), detonating cord has a detonation rate of 6.7 km/s (22,000 feet per second), and C-4 has a detonation rate of about 8.5 km/s (29,000 feet per second).

Some high explosive materials, such as nitrocellulose and nitroglycerine, can be used in propellant mixtures. This is typically done by mixing the high explosive material with other materials that permit the resulting mixture to be cut or shaped. This process allows for a greater amount of control over the reaction to achieve the desired effect as a propellant.

A low explosive material, on the other hand, reacts at a rate slower than the speed of sound. Low explosives can react at rates from a few centimeters per minute to approximately 400 meters per second. Low explosives can be used to produce large volumes of gas in a controllable manner, which is why one common use for low explosives is as a propellant. Examples of low explosive materials include smokeless and black gun powder, and the like.

An explosive material can further be characterized as a primary or initiating explosive material or a secondary explosive material based on its susceptibility to initiation. A primary explosive material is more sensitive to ignition and is typically used to set off the secondary explosive material, which is less sensitive but explodes violently when ignited. The primary explosive material is generally used in small quantities to ignite larger quantities of the secondary explosive material. The primary explosive material can be ignited by a spark, friction, or impact. Examples of primary explosive materials include lead azide, lead styphnate, mercury fulminate, tetrazene, diazodinitrophenol, and the like.

A primary explosive material can be used in detonators, fuzes, blasting caps, and percussion caps to ignite the secondary explosive material. A small quantity of the primary explosive material, usually milligrams, is sufficient to ignite a larger charge of the secondary explosive material that is usually safer to handle.

TABLE 2

Examples of Primary Explosive Materials

Acetone peroxide

Alkali metal ozonides
Ammonium permanganate
Ammonium chlorate
Azidotetrazolates
Azo-clathrates
Benzoyl peroxide
Benzvalene
Chlorine oxides
Copper(I) acetylide
Copper(II) azide
Cumene hydroperoxide
Cyanogen azide
Cyanuric triazide
Diacetyl peroxide
1-Diazidocarbamoyl-5-azidotetrazole
Diazodinitrophenol
Diazomethane
Diethyl ether peroxide
4-Dimethylaminophenylpentazole
Disulfur dinitride
Ethyl azide
Explosive antimony
Fluorine perchlorate
Fulminic acid
Halogen azides:
   Fluorine azide
   Chlorine azide
   Bromine azide
Hexamethylene triperoxide diamine
Hydrazoic acid
Hypofluorous acid
Lead azide
Lead styphnate
Lead picrate [13]
Manganese heptoxide
Mercury(II) fulminate
Mercury nitride
Methyl ethyl ketone peroxide
Nickel hydrazine nitrate
Nickel hydrazine perchlorate
Nitrogen trihalides:
   Nitrogen trichloride
   Nitrogen tribromide
   Nitrogen triiodide
Nitroglycerin
Nitronium perchlorate
Octaazacubane
Pentazenium hexafluoroarsenate
Peroxy acids
Peroxymonosulfuric acid
Selenium tetraazide
Silicon tetraazide
Silver azide
Silver acetylide
Silver fulminate
Silver nitride
Sodium azide
Tellurium tetraazide
tert-Butyl hydroperoxide
Tetraamine copper complexes
Tetraazidomethane
Tetrazene explosive
Tetranitratoxycarbon
Tetrazoles
Titanium tetraazide
Triazidomethane
Xenon dioxide
Xenon oxytetrafluoride
Xenon tetroxide The secondary explosive materials can be schematically divided into two groups: booster or auxiliary explosive material and main charge, bursting, or filler explosive material. Booster explosive material is used to increase the flame or shock of the primary explosive material to ensure a stable detonation in the main charge explosive material. High explosive material used as the booster explosive is less sensitive than the explosive material used in initiators, primers, and detonators, but are more sensitive than those used as the main charge explosive material. Examples of booster explosive material includes RDX, tetryl, PETN, and the like.

The main charge explosive material is the explosive material that forms the principal explosive charge in various types of explosive ordnance 200 such as mines, bombs, missiles, projectiles, and the like. The main charge explosive material is typically a high explosive material, Examples of main charge explosive material includes TNT, RDX compositions, HMX, Explosive D, and the like.

As mentioned above, the secondary explosive material is less sensitive than a primary explosive material and requires substantially more energy to ignite. Because they are less sensitive, the secondary explosive material can be used in a wider variety of applications and are safer to handle and store. A secondary explosive material is used in larger quantities in the explosive train and is usually ignited by a smaller quantity of a primary explosive material.

It should be appreciated that the categories and descriptions of the various explosive materials are not mutually exclusive. For example, one explosive material may be suitable for use as a booster explosive material in one context and a main charge explosive material in another context.

Propellant is a form of energetic material 204 that can be used to provide controlled propulsion for projectiles such as bullets, mortar rounds, artillery rounds, rockets, missiles, and the like. Because the projectile must be directed with respect to range and direction, the explosive process is restrained. In order to allow a controlled rate of reaction that that is slower than that of an actual detonation, the physical properties of the propellant, such as the grain size and form, are carefully controlled.

Historically, the first propellant used was black powder. Modern gun propellants consist of one or more explosive materials and additives. These gun propellants are often referred to as "smokeless powders" to distinguish these materials from black powder. They are largely smokeless on firing compared to black powder, which gives off more than 50 percent of its weight as solid products. In addition to chemical formulation of gun powder, the development of gun powder consisting of denser and larger grains of fixed geometric shapes permitted greater control of a gun's ballistic effects.

Most, if not all, solid gun propellants contain nitrocellulose. As a nitrated natural polymer, nitrocellulose has the requisite mechanical strength and resilience to maintain its integrity during handling and firing. Nitrocellulose is partially soluble in some organic solvents. These solvents include acetone, ethanol, ether/ethanol, and nitroglycerine. When a mixture of nitrocellulose and solvent is worked, a gel forms. This gel retains the strength of the polymer structure of nitrocellulose. Other propellant ingredients include nitroglycerine and nitroguanidine.

There are three compositions of gun propellants: single-base, double-base, and triple-base. A single-base propellant contains nitrocellulose as its primary explosive material or ingredient. Some compositions contain dinitrotoluenes (DNTs) as well. Single-base propellants are used in all manner of guns, from pistols to artillery. A double-base propellant contains nitroglycerine in addition to nitrocellulose. The amount of nitroglycerine present is lower now than when double-base propellants were introduced because modern automatic weapons are eroded by the hotter gases produced by propellants having higher amounts of nitroglycerine. Double-base propellants are largely used in ammunition for pistols and submachine guns. Triple-base propellants contain up to 55 percent by weight of nitroguanidine, as well as nitrocellulose and a small amount of nitroglycerine. The use of triple-base propellants is especially effective in large guns, because they reduce barrel erosion, extend barrel life, and reduce flash.

Rocket propellants are explosive materials designed to burn smoothly without risk of detonation, thus providing smooth propulsion. Some classes of rocket propellants are similar in composition to the previously described gun propellants. However, due to the different requirements and operating conditions, there are often differences in formulation. Gun propellants have a very short burn time with a high internal pressure. Rocket propellants, on the other hand, typically burn longer and operate at a lower pressure than gun propellants.

Rocket propellants can be liquid or solid. There are two types of liquid propellants: monopropellants, which have a single material, and bipropellants, which have both a fuel and an oxidizer. Currently, the most commonly used monopropellant is hydrazine. Bipropellants are used on powerful launch systems such as space vehicle launchers. One or both of the components could be cryogenic material, such as liquid hydrogen and liquid oxygen. Noncryogenic systems include those used on tactical missiles. Examples of such propellants include unsymmetrical demethylhydrazine. The oxidizer can be a material such as an inhibited fuming nitric acid that contains nitric acid, dinitrogen tetroxide, and 0.5 percent hydrofluoric acid as a corrosion inhibitor.

Unlike the liquid-fueled rocket motors, in which the propellant is introduced into a combustion chamber, the solid fuel motor contains all of its propellant in the combustion chamber. Solid fuel propellants for rocket motors include double-base, modified double-base, and composites. Double-base rocket propellants are similar to the double-base gun propellants discussed earlier. Thus, they consist of a colloidal mixture of nitrocellulose and nitroglycerine with a stabilizer. A typical composition for a double-base propellant consists of nitrocellulose (51.5%), nitroglycerine (43%), diethylphthalate (3%), potassium sulfate (1.25%), ethyl centralite (1%), carbon black (0.2%), and wax (0.05%).

Modified double-base propellants provide higher performance than double-base propellants. Two typical compositions for modified double-base propellants are (a) nitrocellulose (20%), nitroglycerine (30%), triacetin (6%), ammonium perchlorate (11%), aluminum (20%), HMX (11%), and a stabilizer (2%); or (b) nitrocellulose (22%), nitroglycerine (30%), triacetin (5%), ammonium perchlorate (20%), aluminum (21%), and a stabilizer (2%). Composite propellants include a polymer structure and an oxidizer. The oxidizer of choice is ammonium perchlorate.

The biopassivation reactor device 210 can be used to biopassivate explosive ordnance 200 including any of the foregoing energetic materials 204.

Figure 4:
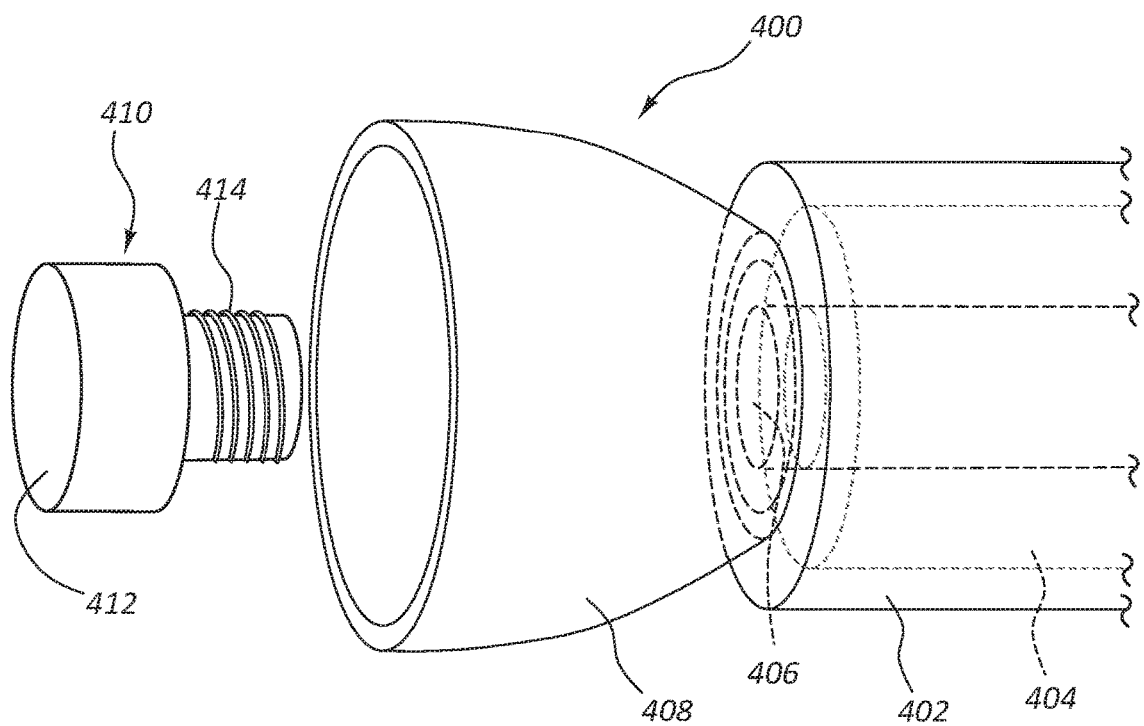
FIGS. 4-5 show perspective views of another embodiment of a biopassivation reactor device that can be coupled to the fuze opening of a solid rocket motor.
Figure 5:
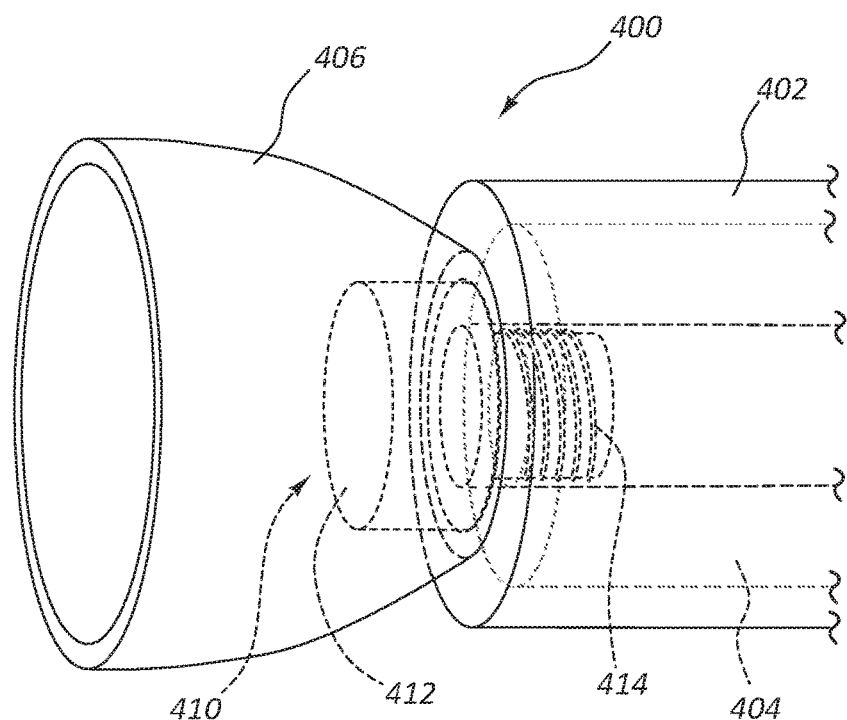

FIGS. 4-5 show perspective views of another embodiment of a biopassivation reactor device 410 configured to be coupled to an explosive ordnance 400. The biopassivation reactor device 410 includes a housing 412 and a coupler 414. The biopassivation reactor device 410 is depicted as being similar or roughly the same as the biopassivation reactor device 210 except that it is likely the device 410 is much larger in scale than the device 210. Accordingly, anything disclosed regarding the device 210 applies equally to the device 410.

The explosive ordnance 400 includes an outer casing 402, energetic material 404, a fuze opening 406, and a nozzle 408. The explosive ordnance 400 is depicted as a solid rocket motor. The biopassivation reactor device 410 is configured to be coupled to the fuze opening 406 of the explosive ordnance 400. The coupler 414 is configured in a manner that is complementary to the fuze opening 406. This makes it possible to fasten the coupler 414 to the fuze opening 406 to provide the microorganisms access to the energetic material 404.

Figure 6:
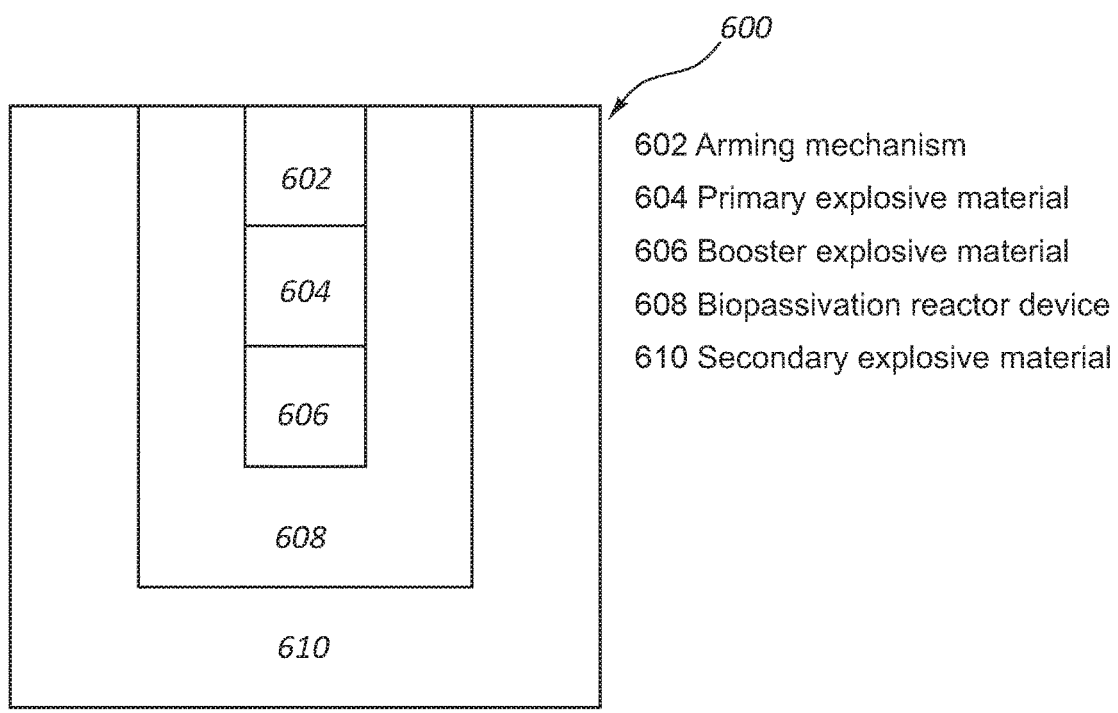
FIG. 6 is a schematic illustration of another embodiment of a biopassivation reactor device incorporated into an explosive mine.
Figure 7:
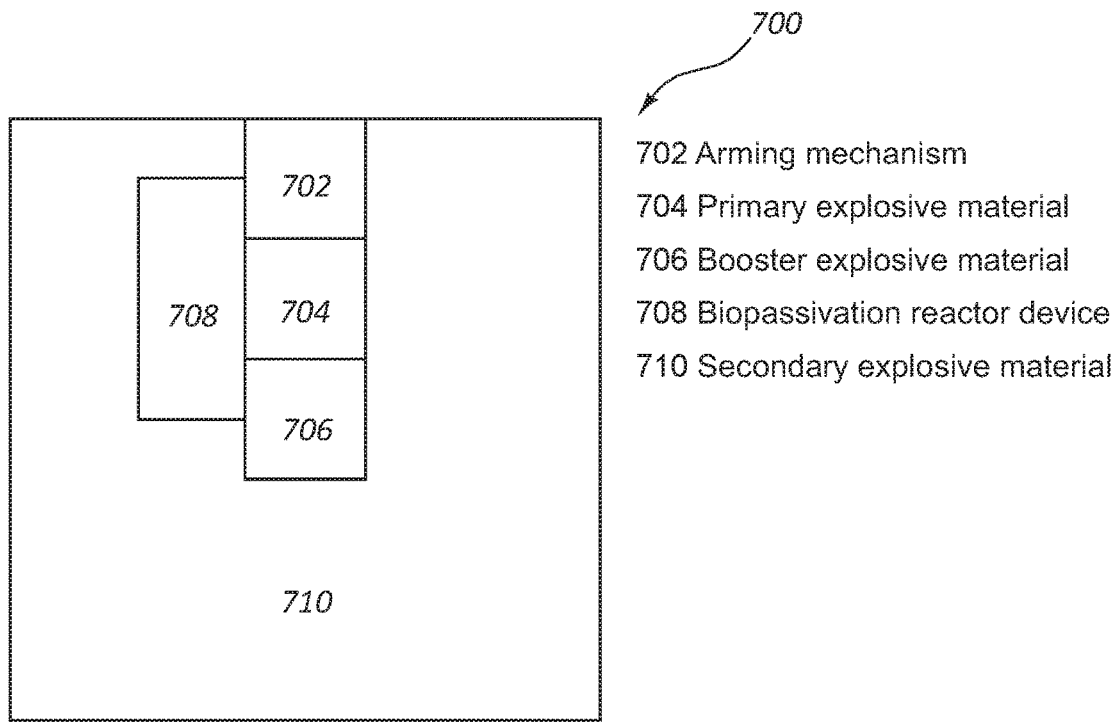
FIG. 7 is a schematic illustration of another embodiment of a biopassivation reactor device incorporated into an explosive mine.

FIGS. 6-7 show schematic illustrations of two explosive ordnances 600, 700 including integrated biopassivation reactor devices 608, 708. The explosive ordnances 600, 700 are shown as landmines but could be other types of explosive ordnances. The explosive ordnances 600, 700 each include, respectively, an arming mechanism 602, 702, a primary explosive material 604, 704 positioned directly below the arming mechanism 602, 702, a booster explosive material 606, 706 positioned directly below the primary explosive material 604, 704 and a secondary explosive material 610, 710. They also each include a biopassivation reactor device 608, 708.

The difference between the embodiments shown in FIGS. 6-7 is that the biopassivation reactor device 608 is positioned between the booster explosive material 606 and the second explosive material 610 in the explosive ordnance 600 while the biopassivation reactor device 708 is positioned mainly in the secondary explosive material 710 to one side of the other explosive materials 704, 708 in the explosive ordnance 700.

In both designs, the biopassivation reactor device 608, 708 is positioned in contact with all form of explosive material in the explosive ordnance 600, 700, respectively. The biopassivation reactor device 608 is positioned in contact with the primary explosive material 604, the booster explosive material 606, and the secondary explosive material 610 in the explosive ordnance 600. Likewise, the biopassivation reactor device 708 is positioned in contact with the primary explosive material 704, the booster explosive material 706, and the secondary explosive material 710.

The biopassivation reactor devices 608, 708 can be configured to operate in any of the ways described above but especially in the ways described above as being particularly suitable for biopassivating mines.

In some embodiments, the microorganisms can be used to passivate an entire ordnance magazine. This may be desirable in situations where the energetic material in the explosive ordnance has chemically degraded to the point that it is unsafe to handle in any way. This can occur when explosive ordnance is stored in an ordnance magazine for a long period of time.

Nitrocellose and related energetic materials are not stable over long periods of time. They decay into compounds that have lower densities than the parent compounds causing the casings of the explosive ordnance to burst. Also, the decay products are often very sensitive to shocks. This creates an extremely dangerous condition for those in the vicinity of the ordnance magazine.

The ordnance magazine can be biopassivated as follows. Microorganisms are initially introduced into the ordnance magazine in any of a number of ways. In some embodiments, the microorganisms are introduced through the ventilation system. For example, they can be blown through the ductwork using fans. The microorganisms can be in the form of dried particles, aerosols, and the like.

The environment inside the ordnance magazine is controlled to facilitate the rapid growth of the microorganisms.

This can involve controlling one or more of a variety of parameters associated with the ordnance magazine such as the temperature, humidity, oxygen level, pH level, liquid waste, and the like. In general, microorganisms thrive in warm, humid conditions where the oxygen level is high and the pH is approximately neutral.

Terminology and Interpretative Conventions

The term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature.

The term "coupled" includes joining that is permanent in nature or releasable and/or removable in nature. Permanent joining refers to joining the components together in a manner that is not capable of being reversed or returned to the original condition. Releasable joining refers to joining the components together in a manner that is capable of being reversed or returned to the original condition.

Releasable joining can be further categorized based on the difficulty of releasing the components and/or whether the components are released as part of their ordinary operation and/or use. Readily or easily releasable joining refers to joining that can be readily, easily, and/or promptly released with little or no difficulty or effort. Difficult or hard to release joining refers to joining that is difficult, hard, or arduous to release and/or requires substantial effort to release. The joining can be released or intended to be released as part of the ordinary operation and/or use of the components or only in extraordinary situations and/or circumstances. In the latter case, the joining can be intended to remain joined for a long, indefinite period until the extraordinary circumstances arise.

It should be appreciated that the components can be joined together using any type of fastening method and/or fastener. The fastening method refers to the way the components are joined. A fastener is generally a separate component used in a mechanical fastening method to mechanically join the components together. A list of examples of fastening methods and/or fasteners are given below. The list is divided according to whether the fastening method and/or fastener is generally permanent, readily released, or difficult to release.

Examples of permanent fastening methods include welding, soldering, brazing, crimping, riveting, stapling, stitching, some types of nailing, some types of adhering, and some types of cementing. Examples of permanent fasteners include some types of nails, some types of dowel pins, most types of rivets, most types of staples, stitches, most types of structural ties, and toggle bolts.

Examples of readily releasable fastening methods include clamping, pinning, clipping, latching, clasping, buttoning, zipping, buckling, and tying. Examples of readily releasable fasteners include snap fasteners, retainer rings, circlips, split pin, linchpins, R-pins, clevis fasteners, cotter pins, latches, hook and loop fasteners (VELCRO), hook and eye fasteners, push pins, clips, clasps, clamps, zip ties, zippers, buttons, buckles, split pin fasteners, and/or conformat fasteners.

Examples of difficult to release fastening methods include bolting, screwing, most types of threaded fastening, and some types of nailing. Examples of difficult to release fasteners include bolts, screws, most types of threaded fasteners, some types of nails, some types of dowel pins, a few types of rivets, a few types of structural ties.

It should be appreciated that the fastening methods and fasteners are categorized above based on their most common configurations and/or applications. The fastening methods and fasteners can fall into other categories or multiple categories depending on their specific configurations and/or applications. For example, rope, string, wire, cable, chain, and the like can be permanent, readily releasable, or difficult to release depending on the application.

Any methods described in the claims or specification should not be interpreted to require the steps to be performed in a specific order unless stated otherwise. Also, the methods should be interpreted to provide support to perform the recited steps in any order unless stated otherwise.

Spatial or directional terms, such as "left," "right," "front," "back," and the like, relate to the subject matter as it is shown in the drawings. However, it is to be understood that the described subject matter may assume various alternative orientations and, accordingly, such terms are not to be considered as limiting.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items.

The terms have, having, include, and including should be interpreted to be synonymous with the terms comprise and comprising. The use of these terms should also be understood as disclosing and providing support for narrower alternative embodiments where these terms are replaced by "consisting" or "consisting essentially of."

Unless otherwise indicated, all numbers or expressions, such as those expressing dimensions, physical characteristics, and the like, used in the specification (other than the claims) are understood to be modified in all instances by the term "approximately." At the very least, and not as an attempt to limit the application of the doctrine of equivalents to the claims, each numerical parameter recited in the specification or claims which is modified by the term "approximately" should be construed in light of the number of recited significant digits and by applying ordinary rounding techniques.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

All disclosed numerical values are to be understood as being variable from 0-100% in either direction and thus provide support for claims that recite such values or any and all ranges or subranges that can be formed by such values. For example, a stated numerical value of 8 should be understood to vary from 0 to 16 (100% in either direction) and provide support for claims that recite the range itself (e.g., 0 to 16), any subrange within the range (e.g., 2 to 12.5) or any individual value within that range (e.g., 15.2).

The drawings shall be interpreted as illustrating one or more embodiments that are drawn to scale and/or one or more embodiments that are not drawn to scale. This means the drawings can be interpreted, for example, as showing: (a) everything drawn to scale, (b) nothing drawn to scale, or (c) one or more features drawn to scale and one or more features not drawn to scale. Accordingly, the drawings can serve to provide support to recite the sizes, proportions, and/or other dimensions of any of the illustrated features either alone or relative to each other. Furthermore, all such sizes, proportions, and/or other dimensions are to be understood as being variable from 0-100% in either direction and thus provide support for claims that recite such values or any and all ranges or subranges that can be formed by such values.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean," etc.). References to specific examples, use of "i.e.," use of the word "invention," etc., are not meant to invoke exception (b) or otherwise restrict the scope of the recited claim terms. Other than situations where exception (b) applies, nothing contained in this document should be considered a disclaimer or disavowal of claim scope.

The subject matter recited in the claims is not coextensive with and should not be interpreted to be coextensive with any embodiment, feature, or combination of features described or illustrated in this document. This is true even if only a single embodiment of the feature or combination of features is illustrated and described in this document.

INCORPORATION BY REFERENCE

With regard to documents incorporated by reference in this specification, if the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

The invention claimed is:

1. A biopassivation reactor device comprising:
   a housing;
   microorganisms enclosed in the housing;
   water enclosed in the housing separately from the microorganisms; and
   a chelating agent enclosed in the housing;
   wherein the microorganisms are capable of biopassivating energetic material in explosive ordnance; and
   wherein the biopassivation reactor device is coupleable to, or integratable into, the explosive ordnance.

2. The biopassivation reactor device of claim 1 wherein the chelating agent is capable of reducing the toxicity of a metal in the energetic material.

3. The biopassivation reactor device of claim 1 wherein the microorganisms are in a deactivated state.

4. The biopassivation reactor device of claim 1 wherein the microorganisms are dehydrated.

5. The biopassivation reactor device of claim 1 wherein the microorganisms are lyophilized.

6. The biopassivation reactor device of claim 1 comprising nutrients enclosed in the housing separately from the microorganisms and the water.

7. The biopassivation reactor device of claim 1 comprising a desiccant enclosed in the housing with the microorganisms.

8. The biopassivation reactor device of claim 1 comprising a controller configured to initiate the biopassivation reactor device by combining the microorganisms, water, and the chelating agent.

9. The biopassivation reactor device of claim 1 wherein the housing comprises:
   a first chamber that includes the microorganisms;
   a second chamber that includes the water; and
   a third chamber that includes the chelating agent.

10. The biopassivation reactor device of claim 1 wherein the biopassivation reactor device is coupleable to a fuze opening of the explosive ordnance.

11. The biopassivation reactor device of claim 10 wherein the housing comprises a coupler couplable to the fuze opening of the explosive ordnance.

12. The biopassivation reactor device of claim 10 wherein the biopassivation reactor device is coupleable to the explosive ordnance in place of a fuze.

13. The biopassivation reactor device of claim 1 comprising the explosive ordnance coupled to the biopassivation reactor device.

14. The biopassivation reactor device of claim 1 wherein the explosive ordnance is a mine.

15. The biopassivation reactor device of claim 1 wherein the explosive ordnance is not unexploded ordnance.

16. The biopassivation reactor device of claim 1 wherein the microorganisms comprise a first microorganism capable of biopassivating energetic material in the explosive ordnance and one or more additional microorganisms that provide syntrophic benefits to the first microorganism.

17. A method comprising activating the biopassivation reactor device of claim 1 by combining the microorganisms and the water, the biopassivation device being coupled to or integrated into the explosive ordnance.

18. The method of claim 17 comprising biopassivating energetic material in the explosive ordnance using the microorganisms.

19. The method of claim 18 wherein the energetic material includes solid rocket motor propellant.

20. The method of claim 17 wherein the biopassivation reactor device comprises at least two microorganisms enclosed in the housing.

21. The method of claim 20 wherein the at least two microorganisms have a syntrophic relationship.

22. The biopassivation reactor device of claim 1 coupled to the explosive ordnance.

23. The biopassivation reactor device of claim 1 integrated into the explosive ordnance.

* * * * *